(12) United States Patent
Hvid et al.

(10) Patent No.: US 12,383,666 B2
(45) Date of Patent: Aug. 12, 2025

(54) CONNECTOR ADAPTED TO ATTACH AN IRRIGATION CATHETER TO TUBING OF AN ANAL OR STOMAL IRRIGATION SYSTEM

(71) Applicant: Coloplast A/S, Humlebaek (DK)

(72) Inventors: Niels Hvid, Vedbaek (DK); Henrik Bay, Lyngby (DK)

(73) Assignee: Coloplast A/S, Humlebaek (DK)

( * ) Notice: Subject to any disclaimer, the term of this patent is extended or adjusted under 35 U.S.C. 154(b) by 522 days.

(21) Appl. No.: 17/715,047

(22) Filed: Apr. 7, 2022

(65) Prior Publication Data
US 2022/0226561 A1    Jul. 21, 2022

Related U.S. Application Data

(63) Continuation of application No. 16/498,395, filed as application No. PCT/DK2018/050072 on Apr. 10, 2018, now Pat. No. 11,324,878.

(30) Foreign Application Priority Data

Apr. 10, 2017 (DK) .......................... PA 2017 70259

(51) Int. Cl.
  *A61M 3/02*   (2006.01)
  *A61M 5/48*   (2006.01)
  *A61M 39/24*  (2006.01)

(52) U.S. Cl.
  CPC .......... *A61M 3/022* (2014.02); *A61M 3/0258* (2013.01); *A61M 3/0279* (2013.01); *A61M 3/0202* (2021.05); *A61M 5/484* (2013.01); *A61M 5/488* (2013.01); *A61M 2039/2413* (2013.01);
  (Continued)

(58) Field of Classification Search
  CPC .............. A61M 3/0258; A61M 3/0279; A61M 2039/2413; A61M 25/10185; A61M 39/10; A61M 2210/1064; A61M 3/02; F16K 17/085
  See application file for complete search history.

(56) References Cited

U.S. PATENT DOCUMENTS

| | | |
|---|---|---|
| 3,902,495 A | 9/1975 | Weiss et al. |
| 4,190,059 A | 2/1980 | Holt |
| 5,190,519 A | 3/1993 | Mead et al. |

(Continued)

FOREIGN PATENT DOCUMENTS

| | | |
|---|---|---|
| CN | 2497129 Y | 6/2002 |
| DE | 202004015358 U1 | 1/2005 |

(Continued)

*Primary Examiner* — Nilay J Shah
(74) *Attorney, Agent, or Firm* — Coloplast Corp., Coloplast A/S; Nick Baumann

(57) ABSTRACT

A connector is disclosed that attaches an irrigation catheter to tubing of an anal or stomal irrigation system. The connector has a housing, a pressure control device retained within the housing, and a restriction element. The pressure control device has an inlet channel on a distal side of the pressure control device communicating along an irrigation flow path with an outlet channel on a proximal side of the pressure control device, and a secondary outlet located between the inlet channel and the outlet channel and in communication with the irrigation flow path. The restriction element is inserted into the secondary outlet.

4 Claims, 7 Drawing Sheets

(52) U.S. Cl.
CPC ............... *A61M 2205/3355* (2013.01); *A61M 2205/502* (2013.01); *A61M 2210/1067* (2013.01)

(56) References Cited

U.S. PATENT DOCUMENTS

| | | |
|---|---|---|
| 5,439,022 A | 8/1995 | Summers et al. |
| 5,788,650 A | 8/1998 | Dotolo |
| 6,106,494 A | 8/2000 | Saravia et al. |
| 6,106,506 A | 8/2000 | Abell et al. |
| 7,955,301 B1 | 6/2011 | McKay |
| 2002/0007156 A1* | 1/2002 | Miles .................... A61M 39/24 604/246 |
| 2007/0093750 A1 | 4/2007 | Jan et al. |
| 2008/0066810 A1* | 3/2008 | Barak .................... A61M 39/24 137/859 |
| 2008/0200871 A1* | 8/2008 | Slater .............. A61M 25/10185 604/96.01 |
| 2009/0254049 A1 | 10/2009 | Adams |
| 2013/0066259 A1 | 3/2013 | Vogel |
| 2014/0194851 A1 | 7/2014 | Burke et al. |
| 2014/0196721 A1* | 7/2014 | Gilhuly ............... A61M 16/209 128/207.15 |
| 2015/0051542 A1 | 2/2015 | Gregory et al. |
| 2017/0274135 A1 | 9/2017 | Frostaa et al. |

FOREIGN PATENT DOCUMENTS

| | | |
|---|---|---|
| RU | 2215545 C1 | 11/2003 |
| WO | 2001008614 A1 | 2/2001 |
| WO | 2016041564 A1 | 3/2016 |

\* cited by examiner

CONNECTOR ADAPTED TO ATTACH AN IRRIGATION CATHETER TO TUBING OF AN ANAL OR STOMAL IRRIGATION SYSTEM

BACKGROUND

Control of voluntary bowel functions is frequently limited or absent in patients suffering from certain disabilities, such as spinal injuries, multiple sclerosis or spina bifida. Such lack of control of voluntary bowel functions typically results in faecal incontinence or intractable constipation, as patients have significantly reduced ability to sense the presence of faeces in the colon terminal part and the rectum and to sense the evacuation stimulus. Patients having undergone stomal surgery wherein a catheterizable stoma is constructed may suffer from similar difficulties.

It is known to accomplish bowel emptying by irrigation (i.e. flushing) of the rectum or stoma, by an irrigating liquid, such as tap water or saline, which is provided through an intermittent catheter with a tip which is configured and sized for insertion into the rectum or stoma, where it remains in a fixed position by an expandable inflation element, such as a balloon. The balloon may be inflatable by air or by water. Once the rectum or stoma has been flushed with the irrigation liquid, the expandable retention element is allowed to collapse to its non-deflated state, allowing the catheter to be withdrawn from the rectum or stoma, and allowing irrigation liquid and faeces to evacuate. The catheter is connected to a reservoir of irrigation liquid through a tube, and a pump may be provided for displacing or pumping irrigation liquid from the reservoir to the catheter.

SUMMARY

There is a need for systems and/or methods increasing the safety for a user of an irrigation system and/or reduce the risk of damage or irritation of a user's bowel during and/or after irrigation.

Accordingly, an adapter for an irrigation system for anal and/or stomal irrigation is disclosed, the adapter comprising a first connector, and a second connector, wherein the first connector and the second connector are connected by a first fluid path for feeding irrigation liquid from the first connector to the second connector, the adapter comprising a pressure control device arranged in the first fluid path, wherein the pressure control device has an inlet side and an outlet side and is configured to keep a liquid pressure on the outlet side less than a first pressure threshold.

Further, an irrigation system for anal and/or stomal irrigation is provided, the irrigation system comprising a reservoir for an irrigation liquid; a tubing system with a first end connectable to the reservoir, and a second end connectable to a catheter and/or an adapter for provision of a first fluid path for the irrigation liquid between the reservoir and the catheter comprising a distal end for expelling irrigation liquid from the catheter; and a pump operable to pump the irrigation liquid from the reservoir to the second end of the tubing system. The irrigation system comprises a mechanical pressure control device, the pressure control device having an inlet side and an outlet side, wherein the inlet side is connected to a reservoir side of the first fluid path and the outlet side is connected to a catheter side of the first fluid path, wherein the pressure control device is configured to keep liquid pressure on the outlet side less than a first pressure threshold.

Also disclosed is a method for operating an irrigation system for anal and/or stomal irrigation, the irrigation system comprising a tubing system with a first end connectable to a reservoir, and a second end connectable to a catheter for provision of a first fluid path for the irrigation liquid between the reservoir and the catheter comprising a distal end for expelling irrigation liquid from the catheter; and an adapter, e.g. as described herein, comprising a first connector, and a second connector, wherein the first connector and the second connector are connected by a first fluid path for feeding irrigation liquid from the first connector to the second connector, the adapter comprising a pressure control device arranged in the first fluid path, wherein the pressure control device has an inlet side and an outlet side and is configured to keep a liquid pressure on the outlet side less than a first pressure threshold. The method comprises coupling the first connector of the adapter to the second end of the tubing system; coupling a catheter to the second connector of the adapter; and pumping irrigation liquid through the first fluid path.

The present disclosure enables more safe anal and/or stomal irrigation by improving the pressure control of the irrigation liquid flow in the irrigation system. The present disclosure enables more effective irrigation while at the same time providing a safe irrigation, by improving the accuracy of fluid pressure control in the irrigation system. Current systems, in order to comply with safety regulations, typically operate with a large safety margin, which in turn reduces the irrigation efficiency in certain use situations. The safety margins applied may result in irrigation liquid pressure at the catheter tip below a desired minimum pressure, e.g. in the range from 1.2 to 1.6 psi, for certain use situations. It is an advantage of the present disclosure that the liquid pressure control is improved, e.g. by increasing the minimum liquid pressure of the irrigation liquid at the catheter tip.

The present disclosure provides a simple, efficient, and easy-to-use irrigation system with a high degree of safety for a user.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
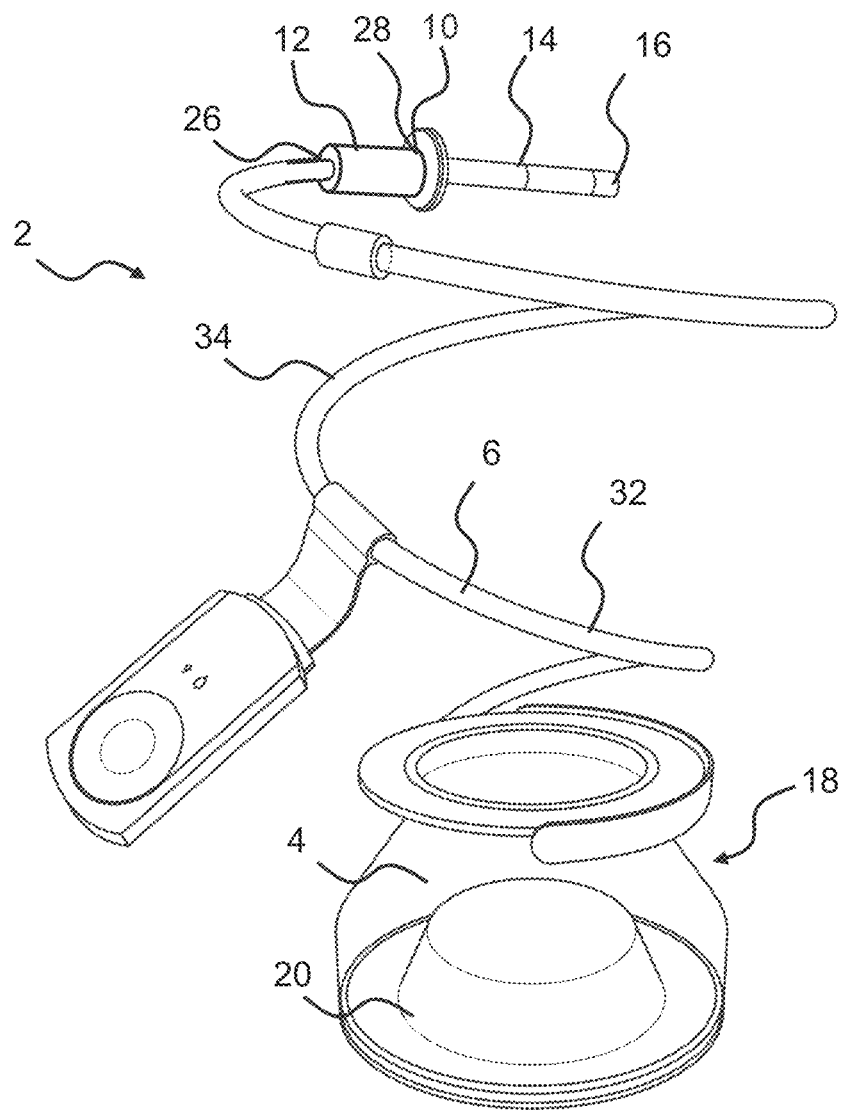
FIG. 1 illustrates an exemplary irrigation system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

An irrigation system for anal and/or stomal irrigation, and an adapter for an irrigation system for anal and/or stomal irrigation is disclosed. The irrigation system may be a point-of-care (POC) irrigation system. A POC irrigation system must be safe to operate with low or no risk of errors, in particular with no risk of self-damaging of a user. The irrigation system may be an irrigation system with no return flow of fluid and faecal material in the tubing system of the irrigation system.

The irrigation system comprises a reservoir for an irrigation liquid. The reservoir may be configured to hold irrigation liquid having a volume of in the range from 100 mL to 3.0 L. In one or more exemplary irrigation systems, the reservoir has a reservoir volume less than 3 L.

The irrigation system comprises a tubing system with a first end and a second end. The first end is optionally connectable or connected to the reservoir and the second end is optionally connectable or connected to a catheter or an adapter for provision of a first fluid path for the irrigation liquid between the reservoir and the catheter comprising a distal end for expelling irrigation liquid from the catheter. The irrigation system may comprise a first fluid path and/or a second fluid path from the first end of the tubing system to the second end of the tubing system. The tubing system may comprise one or more tubing parts, such as a first tubing part and/or a second tubing part, for forming fluid path(s) between different housings of the irrigation system. The tubing system and parts thereof may comprise one or more first channels for forming parts of the first fluid path. The tubing system and parts thereof may comprise one or more second channels for forming parts of a second fluid path. The first fluid path of the irrigation system is for feeding irrigation liquid from the reservoir to the second end of the tubing system, e.g. for irrigating the bowel of the user. The second fluid path of the irrigation system may be for feeding irrigation liquid from the reservoir to the second end of the tubing system. The second fluid path may be for inflating or filling a balloon of the catheter, e.g. with irrigation liquid from the reservoir and/or air.

The tubing system may comprise a first connector at the first end of the tubing system. The tubing system may comprise a second connector at the second end of the tubing system. A tubing system with one or more connectors facilitate the use of different sized tubing system, e.g. to adapt to different users, and/or easy handling of the irrigation system, e.g. disassembly for storing. The second connector may be configured for coupling, e.g. detachable coupling, to a catheter and/or an adapter.

The irrigation system comprises a pump, such as an electrical pump, operable to pump the irrigation liquid from the reservoir to the second end of the tubing system. The pump may be arranged with the reservoir in a reservoir housing.

The irrigation system may comprise a user control interface housing with a user control interface. The user control interface enables a user to control the irrigation system. The user control interface housing may be attached to the tubing system. In one or more exemplary irrigation systems, the pump may be arranged in the user control interface housing.

The irrigation system may comprise a mechanical pressure control device for controlling the fluid pressure of the irrigation liquid. The mechanical pressure control device increases the safety for a user while enabling a sufficiently high fluid pressure at the catheter tip to perform effective irrigation. The pressure control device has an inlet side and an outlet side. The inlet side of the pressure control device is optionally connected to a reservoir side of the first fluid path and the outlet side of the pressure control device is optionally connected to a catheter side of the first fluid path.

The pressure control device may be arranged at a distance less than 50 cm from the second end of the tubing system. The pressure control device may be arranged at a distance less than 30 cm from the second end of the tubing system, such as within 15 cm from the second end of the tubing system. The pressure control device may be arranged in the second connector of the tubing system. The pressure control device may be arranged in a pressure control housing, e.g. at a distance less than 30 cm from the second end of the tubing system.

In one or more exemplary irrigation systems, where the irrigation system comprises a user control interface housing attached to the tubing system, the pressure control device may be arranged in the user control interface housing or between the user control interface housing and the second end of the tubing system.

The adapter comprises a first connector and a second connector. The first connector and the second connector are connected by a first fluid path for feeding irrigation liquid from the first connector to the second connector.

The first connector of the adapter is optionally configured to be attached to an end of a tubing system, such as a second end, e.g. a second connector, of a tubing system of the irrigation system. The second connector of the adapter is optionally configured to be attached to a catheter. The adapter comprises a pressure control device arranged in the first fluid path, wherein the pressure control device has an inlet side and an outlet side and is configured to keep a liquid pressure on the outlet side less than a first pressure threshold.

The first pressure threshold may be in the range from 1.0 Psi to 3.0 Psi. In one or more exemplary irrigation systems and/or adapters, the first pressure threshold may be in the range from 1.6 Psi to 2.2 Psi.

The pressure control device may comprise a pressure regulator comprising a loading element including a first spring. The pressure control device/pressure regulator may comprise a restricting element arranged to vary the fluid flow through the pressure control device. The loading element may comprise a second spring. The pressure regulator may comprise a diaphragm, e.g. as part of the loading element. The loading element is optionally connected to the restricting element for loading and moving the restriction element when liquid flows in through the pressure control device.

The pressure control device may comprise a pressure relief valve comprising a secondary outlet, wherein the pressure relief valve is configured to open the secondary outlet when the liquid pressure in the pressure relief valve or on the outlet side reaches the first threshold pressure. The tubing system and/or the adapter may comprise a tube with a first end, wherein the first end of the tube is connected to the secondary outlet. The pressure relief valve may comprise a restricting element arranged to vary the fluid flow through the secondary outlet. The pressure relief valve may be configured to close the secondary outlet when the liquid pressure in the pressure relief valve is below the first threshold pressure.

A restriction element of the pressure control device may be made of a flexible material, such as rubber or silicone.

The adapter may comprise a second channel forming a part of a second fluid path and connecting the first connector and the second connector for feeding second fluid from the first connector to the second connector. Thus, feeding of a second fluid such as gas/air or liquid from the tubing system to the catheter is provided for, e.g. in order to inflate or fill soft inflatable balloon of the catheter in order to keep the catheter in place during irrigation.

The adapter may comprise a housing made of a plastic material, such as polypropylene or polyethylene. The adapter housing may be an elongate housing, e.g. with the first connector arranged at a first end of the adapter housing and/or with the second connector arranged at a second end of the adapter housing. The adapter housing may have a length or maximum extension along a longitudinal axis in the range from 1 cm to 15 cm. The adapter housing may have a width or maximum extension perpendicular to the longitudinal axis in the range from 1 cm to 5 cm.

FIG. 1 shows an exemplary irrigation system for anal and/or stomal irrigation. The irrigation system 2 comprises a reservoir 4 for an irrigation liquid; a tubing system 6 with a first end 8 (not shown in FIG. 1) connectable to the reservoir 4, and a second end 10 with a second connector 12 connectable to a catheter 14 for provision of a first fluid path for the irrigation liquid between the reservoir 4 and the catheter 14 comprising a distal end 16 for expelling irrigation liquid from the catheter 16. The irrigation system 2 comprises a pump operable to pump the irrigation liquid from the reservoir 4 to the second end 10 of the tubing system 6. The pump is optionally arranged in reservoir housing 18 with reservoir 4, such as in bottom part 20 of the reservoir housing 18.

The irrigation system 2 comprises a mechanical pressure control device 22 (See FIG. 3) arranged in the second connector 12. The pressure control device has an inlet side 26 and an outlet side 28, wherein the inlet side 26 is connected to a reservoir side of the first fluid path and the outlet side 28 is connected to a catheter side of the first fluid path, wherein the pressure control device 22 is configured to keep liquid pressure on the outlet side 28 less than a first pressure threshold of in the range from 1.6 Psi to 2.2 Psi. The tubing system 6 comprises a first tubing part 32 and a second tubing part 34 each forming a part of the first fluid path of the irrigation system. The first tubing part 32 extends between the reservoir housing 18 and a user control interface housing 30 attached to the tubing system 6. The second tubing part 34 extends between the user control interface housing 30 (See FIG. 2) and the pressure control device 22/second connector 12.

Figure 2:
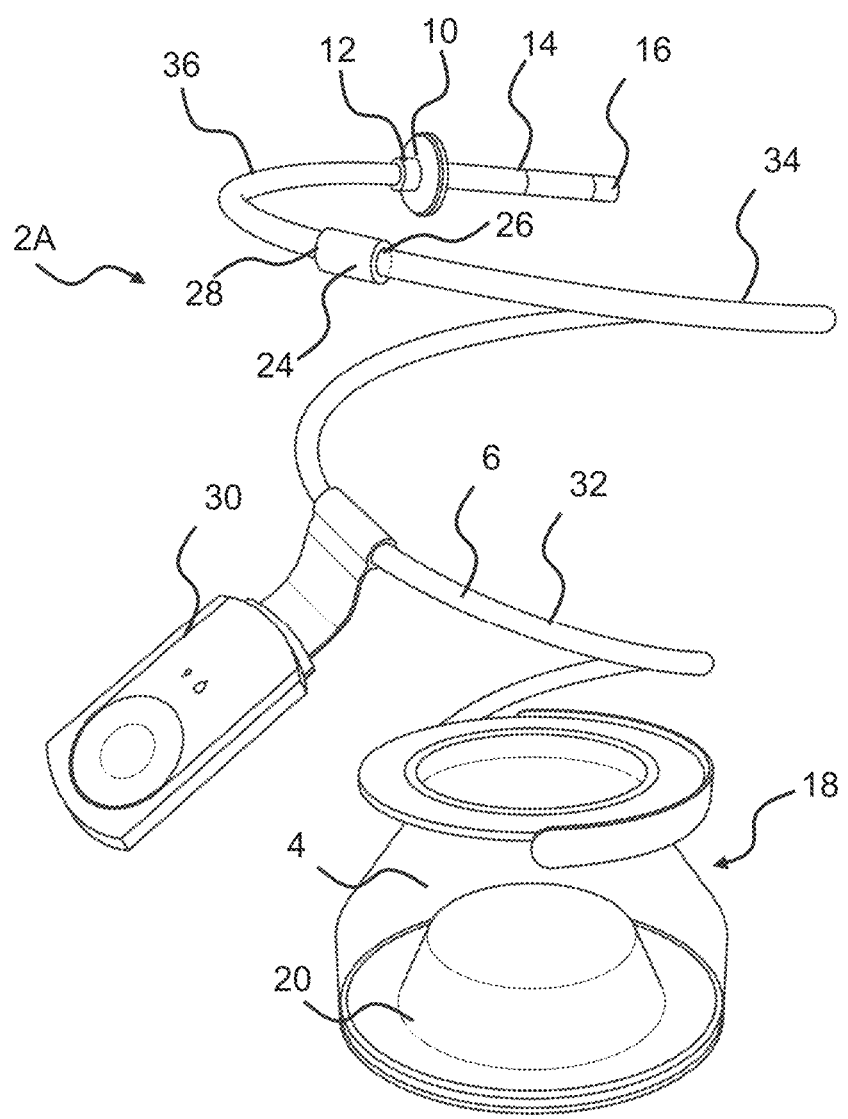
FIG. 2 illustrates an exemplary irrigation system.

FIG. 2 shows an exemplary irrigation system for anal and/or stomal irrigation. The irrigation system 2A comprises a reservoir 4 for an irrigation liquid; a tubing system 6 with a first end 8 (not shown in FIG. 1) connectable to the reservoir 4, and a second end 10 with a second connector 12 connectable to a catheter 14 for provision of a first fluid path for the irrigation liquid between the reservoir 4 and the catheter 14 comprising a distal end 16 for expelling irrigation liquid from the catheter 16. The irrigation system 2A comprises a pump operable to pump the irrigation liquid from the reservoir 4 to the second end 10 of the tubing system 6. The pump is optionally arranged in the bottom part 20 of the reservoir housing 18. The irrigation system 2A comprises a mechanical pressure control device 22 (See FIG. 3) arranged in a pressure control housing 24 at a distance of 20 cm, i.e. less than 50 cm, from the second end 10 of the tubing system 6. The distance is measured along the first fluid path. The pressure control device has an inlet side 26 and an outlet side 28, wherein the inlet side 26 is connected to a reservoir side of the first fluid path and the outlet side is connected to a catheter side of the first fluid path, wherein the pressure control device 22 is configured to keep liquid pressure on the outlet side 28 less than a first pressure threshold of in the range from 1.6 Psi to 2.2 Psi. The irrigation system 2A comprises a user control interface housing 30 attached to the tubing system 6, wherein the pressure control device 22 is arranged between the user control interface housing 30 and the second end 10 of the tubing system. The tubing system 6 comprises first tubing part 32, second tubing part 34, and a third tubing part 36 each forming a part of the first fluid path of the irrigation system. The first tubing part 32 extends between the reservoir housing 18 and the user control interface housing 30. The second tubing part 34 extends between the user control interface housing 30 and the pressure control device 22, and the third tubing part 36 extends between the pressure control device 22 and the second end 10 of the tubing system. The length of the third tubing part is less than 50 cm, such as less than 30, e.g. about 20 cm.

Figure 3:
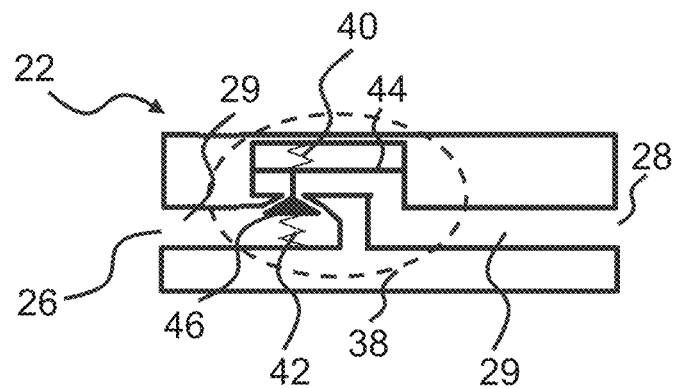
FIG. 3 illustrates an exemplary pressure control device.

FIG. 3 illustrates a cross-section of an exemplary pressure control device. The pressure control device 22 has an inlet side 26 and an outlet side 28, wherein the inlet side 26 is connected or connectable to a reservoir side of the first fluid path 29 and the outlet side is connected or connectable to a catheter side of the first fluid path, wherein the pressure control device is configured to keep liquid pressure on the outlet side less than a first pressure threshold. The pressure control device 22 comprises a pressure regulator 38 comprising a loading element including a first spring 40, a second spring 42, and a diaphragm 44. The pressure regulator 38 comprises a valve or restriction element 46. A poppet valve forms the restriction element 46. Other suitable valves may be used as a restriction element. The second spring 42 on the inlet side and the first spring 40 and the diaphragm 44 on the outlet side adjusts the valve opening size such that liquid pressure on the outlet side 28 is less than a first pressure threshold, such as in the range from 1.6 Psi to 2.2 Psi, e.g. 2.0 Psi.

Figure 4:
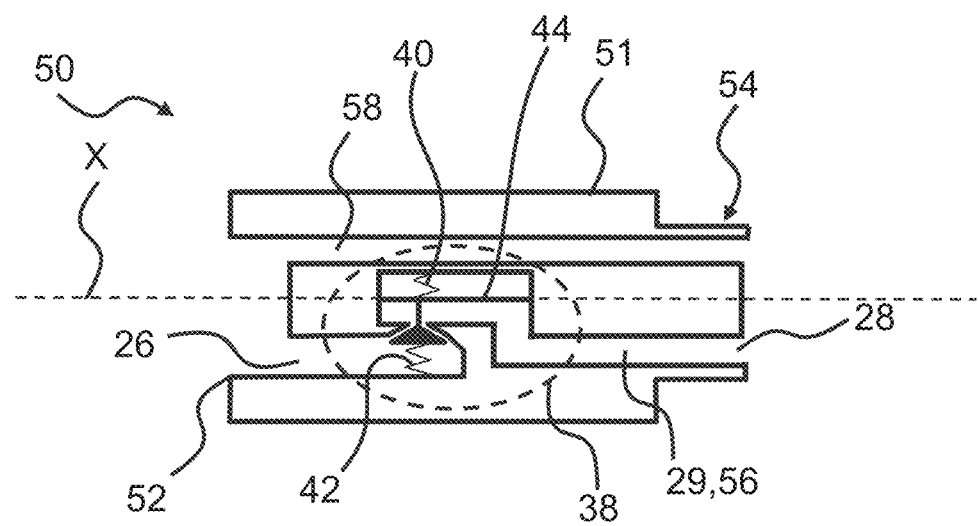
FIG. 4 illustrates an exemplary adapter.

FIG. 4 illustrates a cross-section of an exemplary adapter for an irrigation system for anal and/or stomal irrigation. The adapter 50 has an adapter housing 51 made of a plastic material and comprises a first connector 52, and a second connector 54, wherein the first connector 52 and the second connector 54 are connected by a first channel 56 of first fluid path 29 for feeding irrigation liquid from the first connector to the second connector. The first connector 52 is configured for connection to a second connector 12 at a second end of a tubing system of the irrigation system, see also FIG. 5. The second connector 54 is configured for connection to a catheter. The first connector 52 and the second connector 54 are optionally connected by a second channel 58 for forming part of a second fluid path and feeding second fluid from the first connector to the second connector, e.g. in order to inflate or fill soft inflatable balloon of the catheter in order to keep the catheter in place during irrigation.

The adapter 50 comprises a pressure control device 22 (within dotted oval) arranged in the first fluid path 56. The pressure control device 22 has an inlet side 26 and an outlet side 28 and is configured to keep a liquid pressure on the outlet side less than a first pressure threshold. An exemplary pressure control device is described in further detail above and shown in FIG. 3.

The adapter housing 51 is an elongate housing with the first connector arranged at a first end of the adapter housing and with the second connector arranged at a second end of the adapter housing. The adapter housing 51 has a length or maximum extension along longitudinal axis X of about 2-3 cm.

Figure 5:
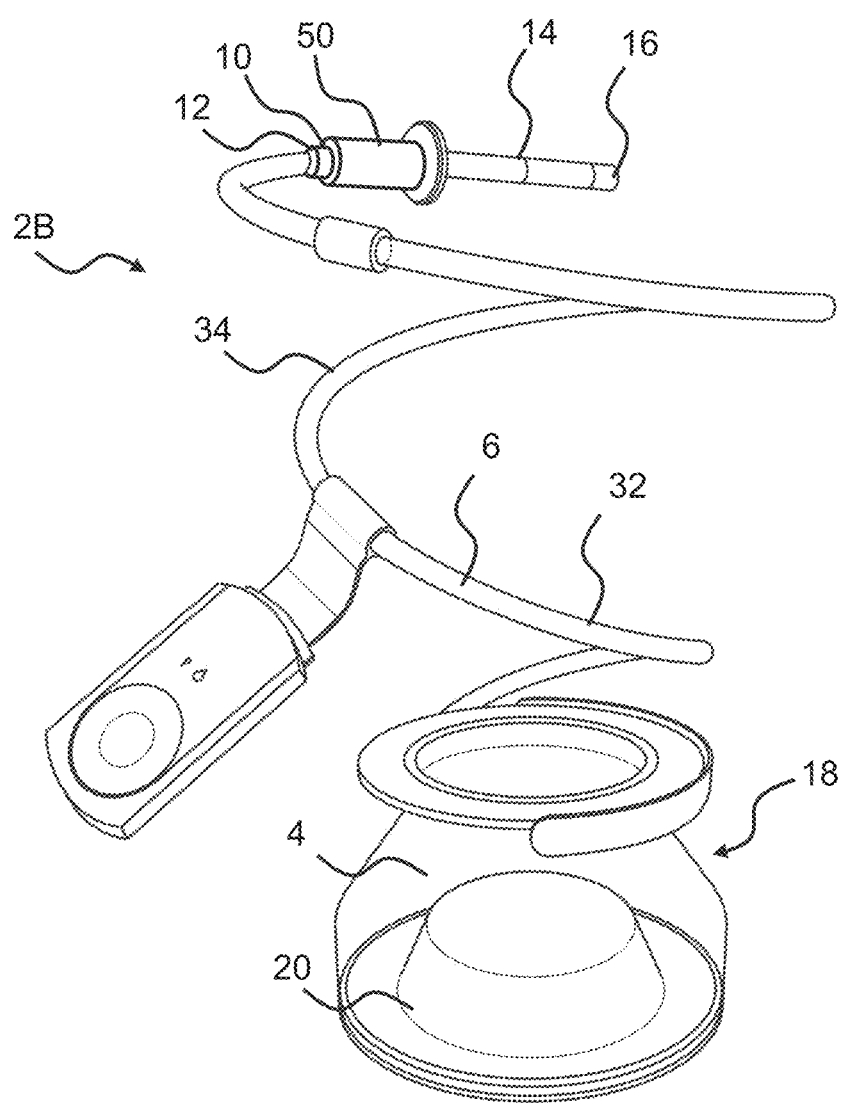
FIG. 5 illustrates an irrigation system with an adapter coupled to the second end of tubing system.

FIG. 5 shows an exemplary irrigation system for anal and/or stomal irrigation with an adapter inserted between the tubing system and the catheter. The irrigation system 2B comprises a reservoir 4 for an irrigation liquid; a tubing system 6 with a first end 8 (not shown in FIG. 5) connectable to the reservoir 4, and a second end 10 with a second connector 12 connected to first connector of adapter 50. Further, second connector of adapter 50 is connected to catheter 14 for provision of a first fluid path for the irrigation liquid between the reservoir 4 and the catheter 14 comprising a distal end 16 for expelling irrigation liquid from the catheter 16. The irrigation system 2B comprises a pump operable to pump the irrigation liquid from the reservoir 4 to the second end 10 of the tubing system 6. The pump is optionally arranged in reservoir housing 20 with reservoir 4, such as in bottom part 20 of the reservoir housing 18. The first tubing part 32 extends between the reservoir housing 18 and the user control interface housing 30. The second tubing part 34 extends between the user control interface housing 30 and the second connector 12.

Figure 6:
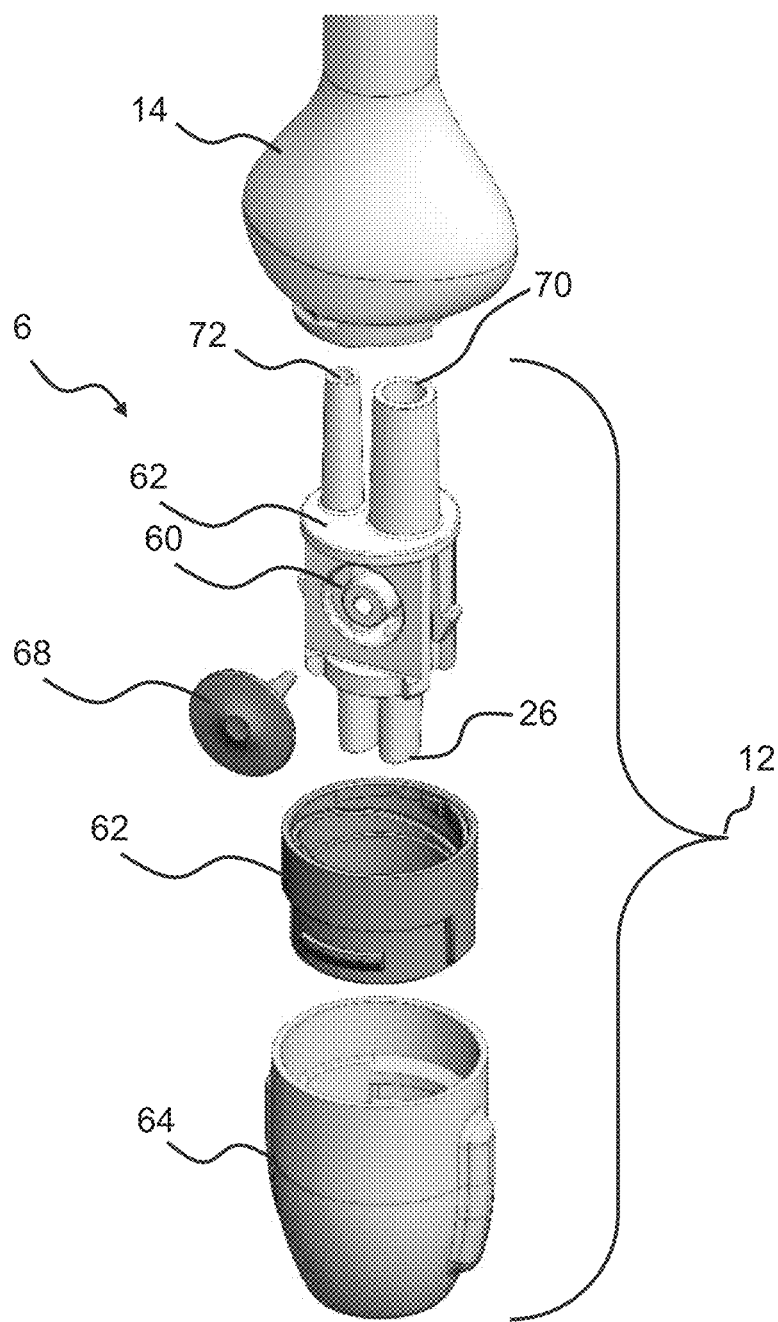
FIG. 6 is an exploded view of parts of an irrigation system.

FIG. 6 shows an exploded view of a second connector of an exemplary tubing system of an irrigation system, and a catheter connectable to the second connector. The second connector 12 comprises a pressure control device in the form of a pressure relief valve. The pressure relief valve comprises a secondary outlet 60 arranged in first connector part 62 of the second connector. The second connector comprises a second connector part 64 and a third connector part 66. The first connector part 62 is, in an assembled second connector, snap-locked to the second connector part 64. The second connector part 64 is, in an assembled second connector, snap-locked to the third connector part 66. The pressure relief valve comprises a restriction element 68 inserted in the first connector part 62. The pressure relief valve is configured to open the secondary outlet when the liquid pressure in the pressure relief valve (first fluid path) reaches the first threshold pressure. The second connector 12 has a first outlet 70 of first fluid path 29 and a second outlet 72 of a second fluid path 74 (if present) of the tubing system 6.

Figure 7:
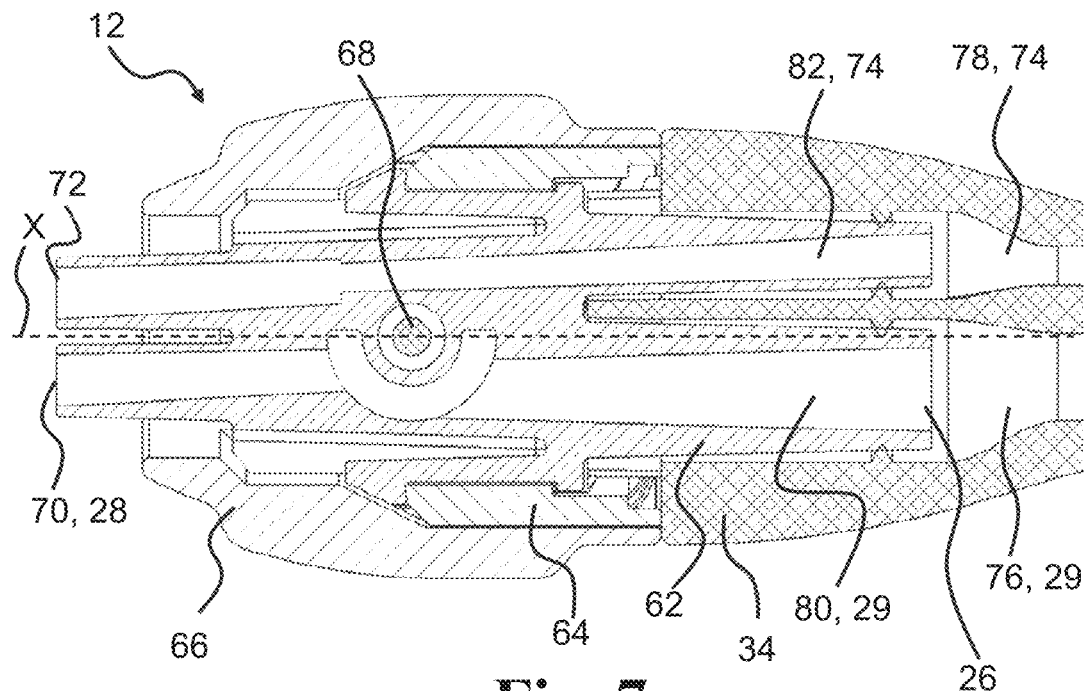
FIG. 7 is a cross section of an exemplary second connector of a tubing system.

FIG. 7 shows a cross-section of the second connector 12 shown in FIG. 6 attached to a tubing part, such as a second tubing part 34 of tubing system 6. A first channel 76 of the second tubing part 34 and first channel 80 of the first connector part 62 forms a part of the first fluid path 29. A second channel 78 of the second tubing part 34 and second channel 82 of the first connector part 62 forms a part of the second fluid path 74. The pressure control device/pressure relief valve has an inlet side 26 and an outlet side 28, wherein the inlet side 26 is connected to a reservoir side of the first fluid path 29 and the outlet side 28 is connected to a catheter side of the first fluid path. The pressure control device 22 is configured to keep liquid pressure on the outlet side 26 less than a first pressure threshold of in the range from 1.6 Psi to 2.2 Psi by allowing irrigation liquid in the first fluid path to bleed out through the secondary outlet if the pressure in the pressure relief valve exceeds a first pressure threshold of in the range from 1.6 Psi to 2.2 Psi. Thus, the pressure relief valve formed by the first connector part 62 and the restriction element 68 is configured to open the secondary outlet 60 when the liquid pressure in the pressure relief valve reaches the first threshold pressure by the flexible restriction element being deformed.

Figure 8:
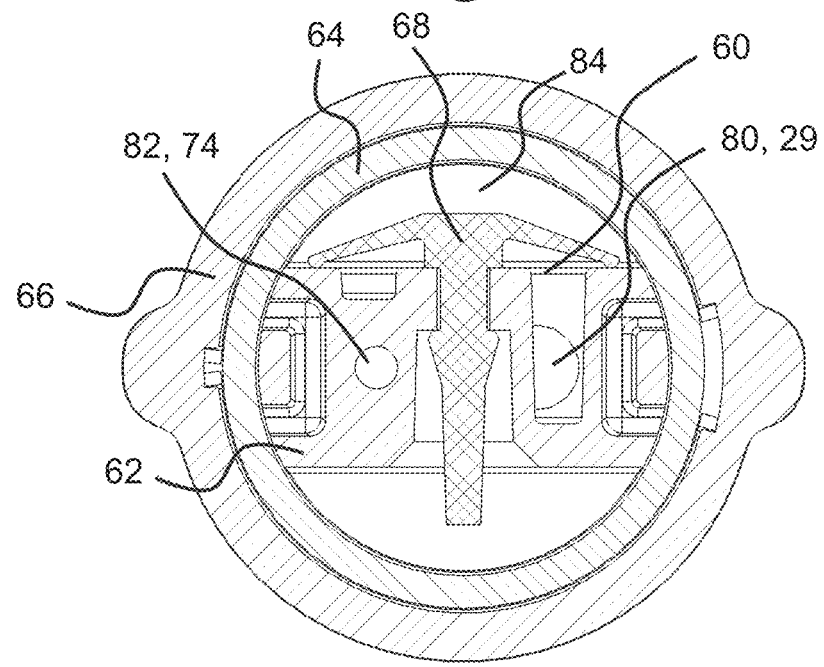
FIG. 8 is a cross section of an exemplary second connector of a tubing system.

FIG. 8 shows a cross-section perpendicular to longitudinal axis X of the second connector 12 shown in FIG. 6. When the liquid/fluid pressure in the first channel 80 is below the first pressure threshold, the restriction element 68 closes the secondary outlet 60. When the liquid/fluid pressure in the first channel 80 reaches the first pressure threshold, the restriction element 68 is deformed allowing irrigation fluid to flow or bleed from the first fluid path through the secondary outlet 60 into the space 84 between first connector part 62 and second connector part 64. When the fluid pressure drops below the first pressure threshold, the restriction element returns to closing the secondary outlet 60.

Figure 9:
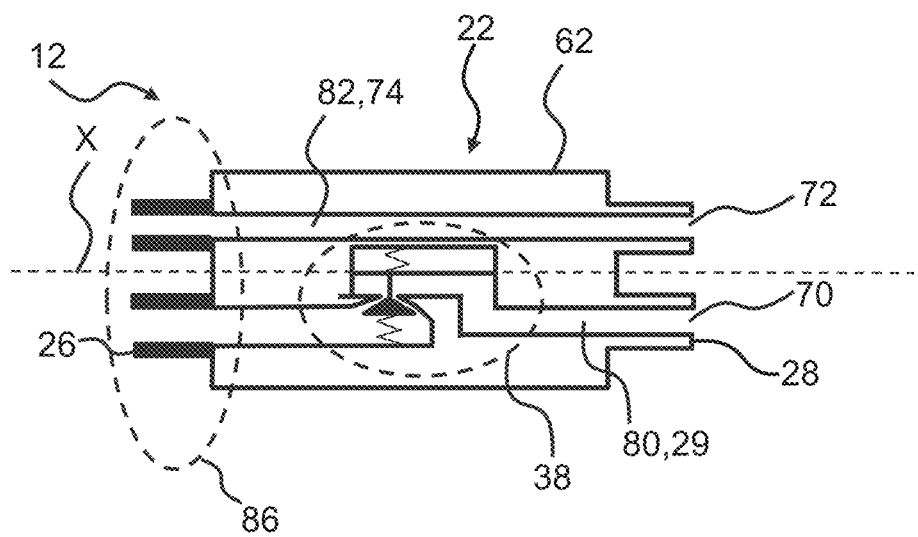
FIG. 9 is a cross section of an exemplary second connector of a tubing system.

FIG. 9 shows a cross-section of an exemplary second connector of the tubing system 6. The second connector 12 comprises a pressure regulator 38 as shown in further detail in FIG. 3 and described in further detail above. A second tubing part (not shown) is attached to the inlet side 86 of the second connector 12 for connecting first and second channels 80,82 of the second connector to respective first and second channels of second tubing part.

Also disclosed are adapters, irrigation systems, and methods according to any of the following items.

Item 1. An adapter for an irrigation system for anal and/or stomal irrigation, the adapter comprising a first connector, and a second connector, wherein the first connector and the second connector are connected by a first fluid path for feeding irrigation liquid from the first connector to the second connector, the adapter comprising a pressure control device arranged in the first fluid path, wherein the pressure control device has an inlet side and an outlet side and is configured to keep a liquid pressure on the outlet side less than a first pressure threshold.

Item 2. Adapter according to item 1, wherein the first pressure threshold is in the range from 1.0 Psi to 3.0 Psi.

Item 3. Adapter according to any of items 1-2, wherein the pressure control device comprises a pressure regulator comprising a loading element including a first spring.

Item 4. Adapter according to any of items 1-3, wherein the pressure control device comprises a pressure relief valve comprising a secondary outlet, wherein the pressure relief valve is configured to open the secondary outlet when the liquid pressure in the pressure relief valve reaches the first threshold pressure.

Item 5. Adapter according to item 4, wherein the adapter comprises a tube with a first end, wherein the first end of the tube is connected to the secondary outlet.

Item 6. Adapter according to any of items 1-5, wherein the adapter comprises a second channel connecting the first connector and the second connector for feeding second fluid from the first connector to the second connector.

Item 7. Adapter according to any of items 1-6, wherein the adapter comprises an adapter housing made of a plastic material.

Item 8. An irrigation system for anal and/or stomal irrigation, the irrigation system comprising:
- a reservoir for an irrigation liquid;
- a tubing system with a first end connectable to the reservoir, and a second end connectable to a catheter or an adapter for provision of a first fluid path for the irrigation liquid between the reservoir and the catheter comprising a distal end for expelling irrigation liquid from the catheter; and
- a pump operable to pump the irrigation liquid from the reservoir to the second end of the tubing system, wherein the irrigation system comprises a mechanical pressure control device, the pressure control device having an inlet side and an outlet side, wherein the inlet side is connected to a reservoir side of the first fluid path and the outlet side is connected to a catheter side of the first fluid path, wherein the pressure control device is configured to keep liquid pressure on the outlet side less than a first pressure threshold.

Item 9. Irrigation system according to item 8, wherein the pressure control device is arranged at a distance less than 50 cm from the second end of the tubing system.

Item 10. Irrigation system according to any of items 8-9, wherein the irrigation system comprises a user control interface housing attached to the tubing system, wherein the pressure control device is arranged in the user control interface housing or between the user control interface housing and the second end of the tubing system.

Item 11. Irrigation system according to any of items 8-10, wherein the first pressure threshold is in the range from 1.0 Psi to 3.0 Psi.

Item 12. Irrigation system according to any of items 8-11, wherein the pressure control device comprises a pressure regulator comprising a loading element including a first spring.

Item 13. Irrigation system according to any of items 8-12, wherein the pressure control device comprises a pressure relief valve comprising a secondary outlet, wherein the pressure relief valve is configured to open the secondary outlet when the liquid pressure on the outlet side reaches the first threshold pressure.

Item 14. Method for operating an irrigation system for anal and/or stomal irrigation, the irrigation system comprising a tubing system with a first end connectable to a reservoir, and a second end connectable to a catheter for provision of a first fluid path for the irrigation liquid between the reservoir and the catheter comprising a distal end for expelling irrigation liquid from the catheter; and an adapter comprising a first connector, and a second connector, wherein the first connector and the second connector are connected by a first fluid path for feeding irrigation liquid from the first connector to the second connector, the adapter comprising a pressure control device arranged in the first fluid path, wherein the pressure control device has an inlet side and an outlet side and is configured to keep a liquid pressure on the outlet side less than a first pressure threshold, the method comprising
- coupling the first connector of the adapter to the second end of the tubing system;
- coupling a catheter to the second connector of the adapter; and
- pumping irrigation liquid through the first fluid path.

Item 15. Method according to item 14, wherein the first pressure threshold is in the range from 1.0 Psi to 3.0 Psi.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 irrigation system
4 reservoir
6 tubing system
8 first end of tubing system
10 second end of tubing system
12 second connector
14 catheter
16 distal end of catheter
18 reservoir housing
20 bottom part
22 pressure control device
24 pressure control housing
26 inlet side of pressure control device
28 outlet side of pressure control device
29 first fluid path
30 user control interface housing
32 first tubing part
34 second tubing part
36 third tubing part
38 pressure regulator
40 first spring
42 second spring
44 diaphragm
46 restriction element
50 adapter
51 adapter housing
52 first connector
54 second connector
56 first channel
58 second channel
60 secondary outlet
62 first connector part
64 second connector part
66 third connector part
68 restriction element
70 first outlet of second connector
72 second outlet of second connector
74 second fluid path
76 first channel of second tubing part
78 second channel of second tubing part
80 first channel of first connector part
82 second channel of first connector part
84 space between first connector part and second connector part
86 inlet side of second connector
X longitudinal axis

What is claimed is:

1. A connector adapted to attach an irrigation catheter to tubing of an anal or stomal irrigation system, the connector comprising:
- a housing comprising a distal portion attachable to the tubing of the anal or stomal irrigation system and a proximal portion attachable to the irrigation catheter;
- a pressure control device retained within the housing, the pressure control device comprising an inlet channel on a distal side of the pressure control device communicating along an irrigation flow path with an outlet channel on a proximal side of the pressure control device, and a secondary outlet located between the inlet channel and the outlet channel and in communication with the irrigation flow path;

a restriction element inserted into the secondary outlet; and an inflation flow path separate from the irrigation flow path, where the inflation flow path is formed through the pressure control device and provides a path for liquid to enter an inflation balloon of the irrigation catheter;

wherein the restriction element of the pressure control device is adapted to open the secondary outlet to limit liquid pressure in the outlet channel to a value less than a pre-determined pressure threshold.

2. The connector of claim 1, wherein the restriction element of the pressure control device is a flexible diaphragm valve that is adapted to deform to form an opening in the secondary outlet to reduce the liquid pressure in the outlet channel.

3. The connector of claim 1, wherein the distal portion of the housing is snap-connected to a perimeter of the pressure control device.

4. A connector adapted to attach an irrigation catheter to tubing of an anal or stomal irrigation system, the connector comprising:

a housing comprising a distal portion attachable to the tubing of the anal or stomal irrigation system and a proximal portion attachable to the irrigation catheter;

a pressure control device retained within the housing, the pressure control device comprising an inlet channel on a distal side of the pressure control device communicating along an irrigation flow path with an outlet channel on a proximal side of the pressure control device, and a secondary outlet located between the inlet channel and the outlet channel and in communication with the irrigation flow path;

an inflation flow path separate from the irrigation flow path, where the inflation flow path is formed through the pressure control device and provides a path for liquid to enter an inflation balloon of the irrigation catheter; and a flexible diaphragm valve inserted into the secondary outlet;

wherein the flexible diaphragm valve is adapted to deform to form an opening in the secondary outlet to reduce liquid pressure at the outlet channel to a value less than a pre-determined pressure threshold of about 1.6 pounds-per-square-inch.

\* \* \* \* \*